(12) United States Patent
Mei et al.

(10) Patent No.: US 11,380,443 B2
(45) Date of Patent: Jul. 5, 2022

(54) PREDICTING NON-COMMUNICABLE DISEASE WITH INFECTIOUS RISK FACTORS USING ARTIFICIAL INTELLIGENCE

(71) Applicant: INTERNATIONAL BUSINESS MACHINES CORPORATION, Armonk, NY (US)

(72) Inventors: Jing Mei, Beijing (CN); Chia Yeow Khiang, Ang Mo Kio (SG); Roslyn Hickson, Fitzroy North (AU); Eryu Xia, Beijing (CN); Shiwan Zhao, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 199 days.

(21) Appl. No.: 16/144,327

(22) Filed: Sep. 27, 2018

(65) Prior Publication Data
US 2020/0105418 A1  Apr. 2, 2020

(51) Int. Cl.
*G16H 50/50* (2018.01)
*G16H 50/70* (2018.01)
(Continued)

(52) U.S. Cl.
CPC ......... *G16H 50/50* (2018.01); *G06F 16/9024* (2019.01); *G06N 20/00* (2019.01); *G06Q 50/01* (2013.01); *G16H 50/70* (2018.01)

(58) Field of Classification Search
CPC ........ G06Q 50/22; G06Q 10/04; G06Q 10/10; G06Q 50/01; Y02A 90/26; G06F 19/00; G06F 16/90328; G06F 19/321; G06F 19/3418; G06F 1/163; G06F 3/00; G06F 3/017; G06F 19/3475; G06F 19/3481; G06F 16/9024; G16B 20/00; G16B 40/00;
(Continued)

(56) References Cited

U.S. PATENT DOCUMENTS

2006/0026298 A1* 2/2006 Zeng .................... G06Q 10/107
709/240
2006/0149674 A1* 7/2006 Cook .................... G06Q 40/02
705/44

(Continued)

OTHER PUBLICATIONS

Christakis, et al., The Collective Dynamics of Smoking in a Large Social Network, The New England Journal of Medicine, May 22, 2008, pp. 2249-2258, vol. 358;21, Massachusetts Medical Society.

(Continued)

*Primary Examiner* — Maroun P Kanaan
(74) *Attorney, Agent, or Firm* — Tutunjian & Bitetto, P.C.; Joseph Petrokaitis (57) ABSTRACT

A computer-implemented method for predicting non-communicable diseases with infectious risk factors using artificial intelligence includes detecting one or more risk factors associated with a non-communicable disease based on a graph associated with person-to-person links, generating a data structure for compactly representing the graph to compute at least one person-to-person distance, and performing a machine learning technique with regularization of the at least one person-to-person distance.

17 Claims, 6 Drawing Sheets

(51) Int. Cl.
  *G06Q 50/00* (2012.01)
  *G06N 20/00* (2019.01)
  *G06F 16/901* (2019.01)
(58) Field of Classification Search
  CPC .......... G16B 5/00; G16B 50/00; G16B 25/00;
    G16H 50/30; G16H 50/20; G16H 50/50;
    G16H 50/70; G16H 10/60; G16H 30/20;
    G16H 30/40; G16H 70/60; C12Q 1/6883;
    C12Q 1/6886; C12Q 2600/118; G06N
    20/00
  See application file for complete search history.

(56) References Cited

U.S. PATENT DOCUMENTS

| 2013/0031179 | A1 | 1/2013 | Christakis et al. |
| 2014/0095184 | A1 | 4/2014 | Gotz et al. |
| 2016/0048634 | A1* | 2/2016 | Torkamani .............. G06F 16/16 707/740 |
| 2016/0283679 | A1 | 9/2016 | Hu et al. |
| 2017/0140123 | A1 | 5/2017 | Ragusa |
| 2017/0329924 | A1* | 11/2017 | Macpherson .......... G16B 20/20 |
| 2019/0205736 | A1* | 7/2019 | Bleiweiss ................ G06N 3/08 |

OTHER PUBLICATIONS

Zion et al., Handling Non Communicable Disease Using Predictive Analysis of Data Mining Techniques, HELIX Scientific Explorer, Sep. 1, 2017, pp. 2034-2041, vol. 7(5).

Thankappan et al., Risk factor profile for chronic non-communicable diseases: Results of a community-based study in Kerala, India, India Journal of Medicine, Jan. 2010, pp. 53-63, vol. 131, Achutha Menon Centre for Health Science Studies, Sree Chitra Tirunal Institute for Medical Sciences and Technology, Thiruvananthapuram 695 011, India.

* cited by examiner

| Gender | Age | Smoking | Obesity | Diabetes |
|--------|-----|---------|---------|----------|
| Male | 55 | Yes | No | Yes |
| Female | 16 | No | No | No |

PREDICTING NON-COMMUNICABLE DISEASE WITH INFECTIOUS RISK FACTORS USING ARTIFICIAL INTELLIGENCE

BACKGROUND

Technical Field

The present invention generally relates to artificial intelligence and machine learning, and more particularly to predicting non-communicable disease with infectious risk factors using artificial intelligence.

Description of the Related Art

Non-communicable diseases (NCDs) can have a genetic basis, or can develop during life based on risk factors. Such risk factors can include, but are not limited to, tobacco use, alcohol, obesity, high blood pressure and/or cholesterol, high blood sugar, physical inactivity, etc. Examples of non-communicable diseases include, but are not limited to, diabetes, cancers, cataracts, fibromyalgia, autoimmune diseases, cardiovascular diseases (e.g., heart attack and stroke), chronic respiratory diseases (e.g., asthma, cystic fibrosis and chronic obstructive pulmonary disease (COPD)), chronic kidney disease, Alzheimer's disease, etc. Non-communicable diseases are known to be the leading cause of death worldwide.

SUMMARY

In accordance with an embodiment of the present invention, a computer-implemented method for predicting non-communicable diseases with infectious risk factors using artificial intelligence is provided. The method includes detecting one or more risk factors associated with a non-communicable disease based on a graph associated with person-to-person links, generating a data structure for compactly representing the graph to compute at least one person-to-person distance, and performing a machine learning technique with regularization of the at least one person-to-person distance.

In accordance with another embodiment of the present invention, a system for predicting non-communicable diseases with infectious risk factors using artificial intelligence is provided. The system includes a memory device for storing program code and at least one processor operatively coupled to the memory device. The at least one processor is configured to execute program code stored on the memory device to detect one or more risk factors associated with a non-communicable disease based on a graph associated with person-to-person links, generate a data structure for compactly representing the graph to compute at least one person-to-person distance, and perform a machine learning technique with regularization of the at least one person-to-person distance.

In accordance with yet another embodiment of the present invention, a computer program product is provided. The computer program product includes a non-transitory computer readable storage medium having program code embodied therewith. The program code are executable by a computer to cause the computer to perform a method for predicting non-communicable diseases with infectious risk factors using artificial intelligence. The method performed by the computer includes detecting one or more risk factors associated with a non-communicable disease based on a graph associated with person-to-person links, generating a data structure for compactly representing the graph to compute at least one person-to-person distance, and performing a machine learning technique with regularization of the at least one person-to-person distance.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Currently, infectious diseases (IDs) and non-communicable diseases (NCDs) are disjoint. The embodiments describe herein provide for precision model to address NCD risk prediction with person-to-person spread of risk factors. For example, obesity can be considered a risk factor for the NCD known as diabetes. Although obesity is not spread through a virus per se, obesity can be considered an "infectious" feature spread via social ties. For example, if a parent is overweight and cooks for a child, the parent may "infect" the child with obesity, which can increase the child's risk of diabetes. Accordingly, obesity can be considered to be an example of an "infectious" feature that can "spread" from person-to-person.

To address NCD risk prediction with person-to-person spread of risk factors, the embodiments described herein can illustratively employ metric learning corresponding to at least one "infectious" risk factor associated with an NCD to generate an adjacency matrix for the at least one "infectious" risk factor. Then, a graph-based machine learning technique, such as, e.g., graph-based supervised learning, can be used, where labels can be smoothed over a graph by using graph-based regularization. Weighting factors can be calculated according to the number of the adjacency matrix.

Figure 1:
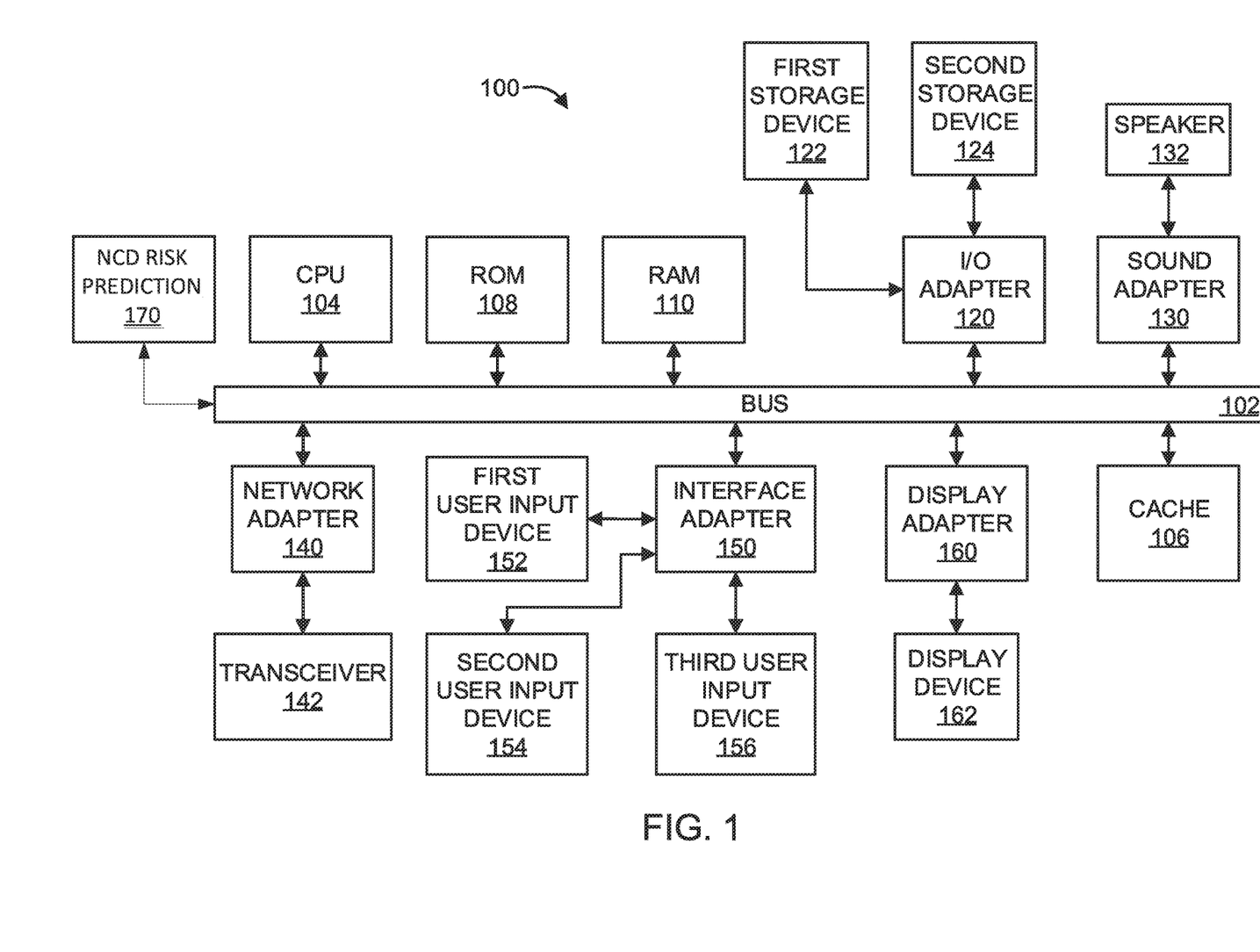
FIG. 1 is a block diagram of a processing system in accordance with an embodiment of the present invention.

Referring now to the drawings in which like numerals represent the same or similar elements and initially to FIG. 1, an exemplary processing system 100 to which the present invention may be applied is shown in accordance with one embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

NCD risk prediction component, or NCD risk predictor, 170 may be operatively coupled to system bus 102. NCD risk prediction component 170 is configured to perform one or more of the operations described below. NCD risk prediction component 170 can be implemented as a standalone special purpose hardware device, or may be implemented as software stored on a storage device. In the embodiment in which NCD risk prediction component 170 is software-implemented, although shown as a separate component of the computer system 100, NCD risk prediction component 170 can be stored on, e.g., the first storage device 122 and/or the second storage device 129. Alternatively, NCD risk prediction component 170 can be stored on a separate storage device (not shown).

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 2:
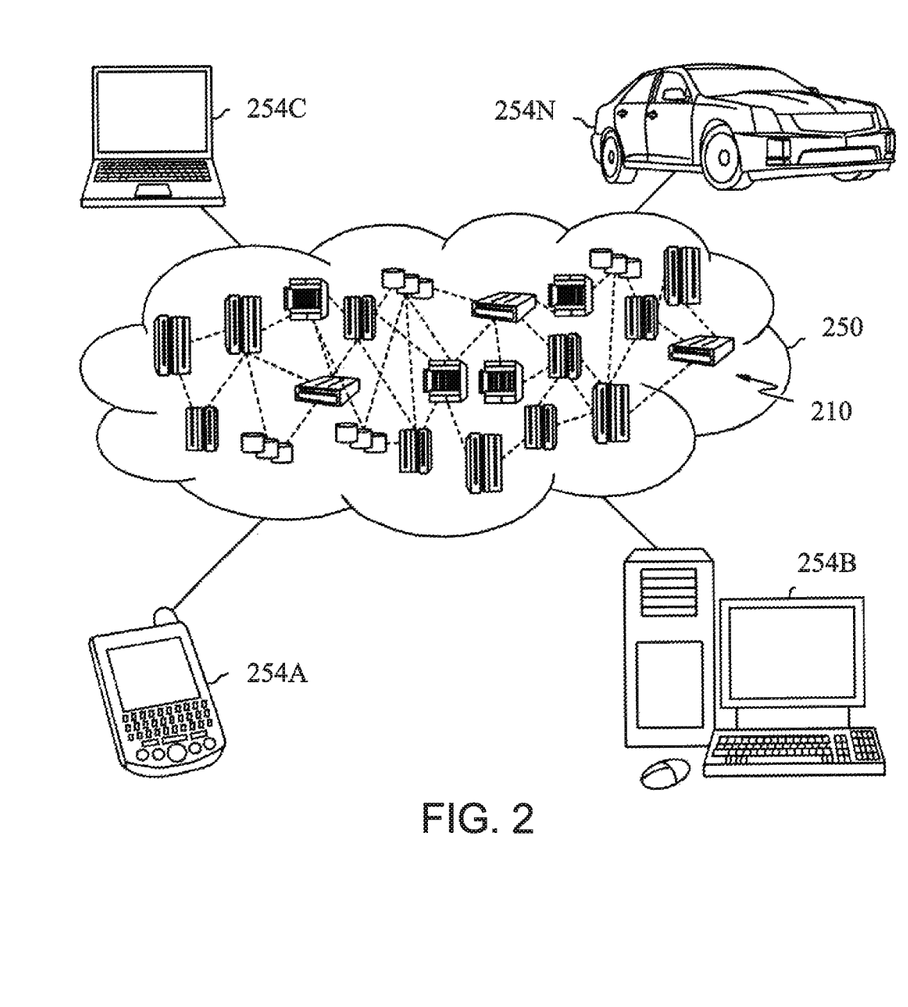
FIG. 2 is a block diagram showing an illustrative cloud computing environment having one or more cloud computing nodes with which local computing devices used by cloud consumers communicate in accordance with an embodiment.

Referring now to FIG. 2, illustrative cloud computing environment 250 is depicted. As shown, cloud computing environment 250 includes one or more cloud computing nodes 210 with which local computing devices used by cloud consumers, such as, for example, personal digital assistant (PDA) or cellular telephone 254A, desktop computer 254B, laptop computer 254C, and/or automobile computer system 254N may communicate. Nodes 210 may communicate with one another. They may be grouped (not shown) physically or virtually, in one or more networks, such as Private, Community, Public, or Hybrid clouds as described hereinabove, or a combination thereof. This allows cloud computing environment 150 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
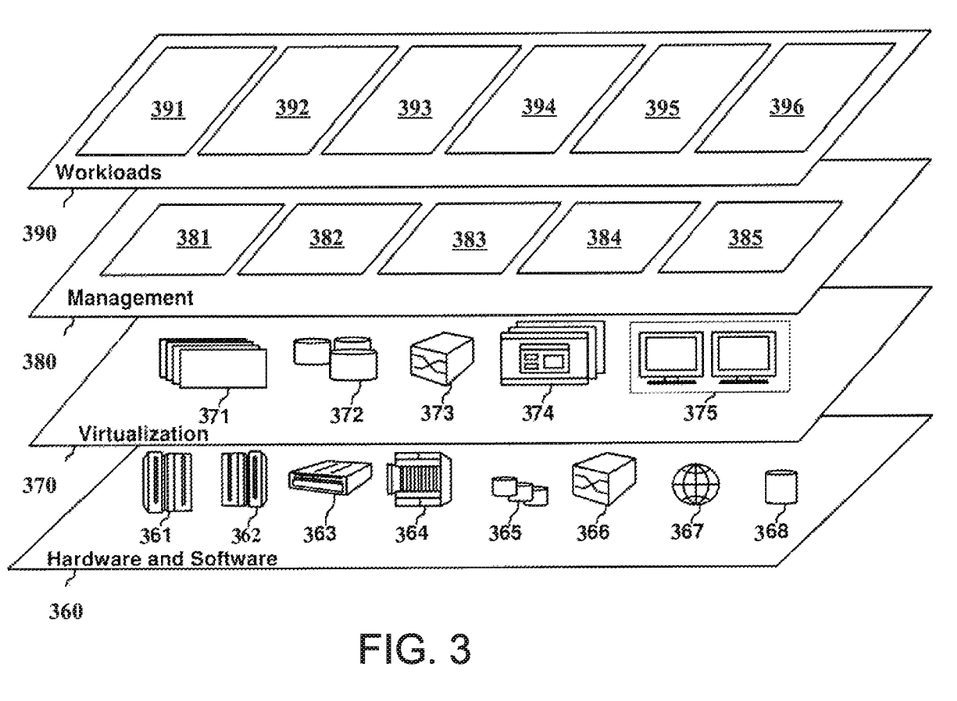
FIG. 3 is a block diagram showing a set of functional abstraction layers provided by a cloud computing environment in accordance with one embodiment.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and machine learning 396.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
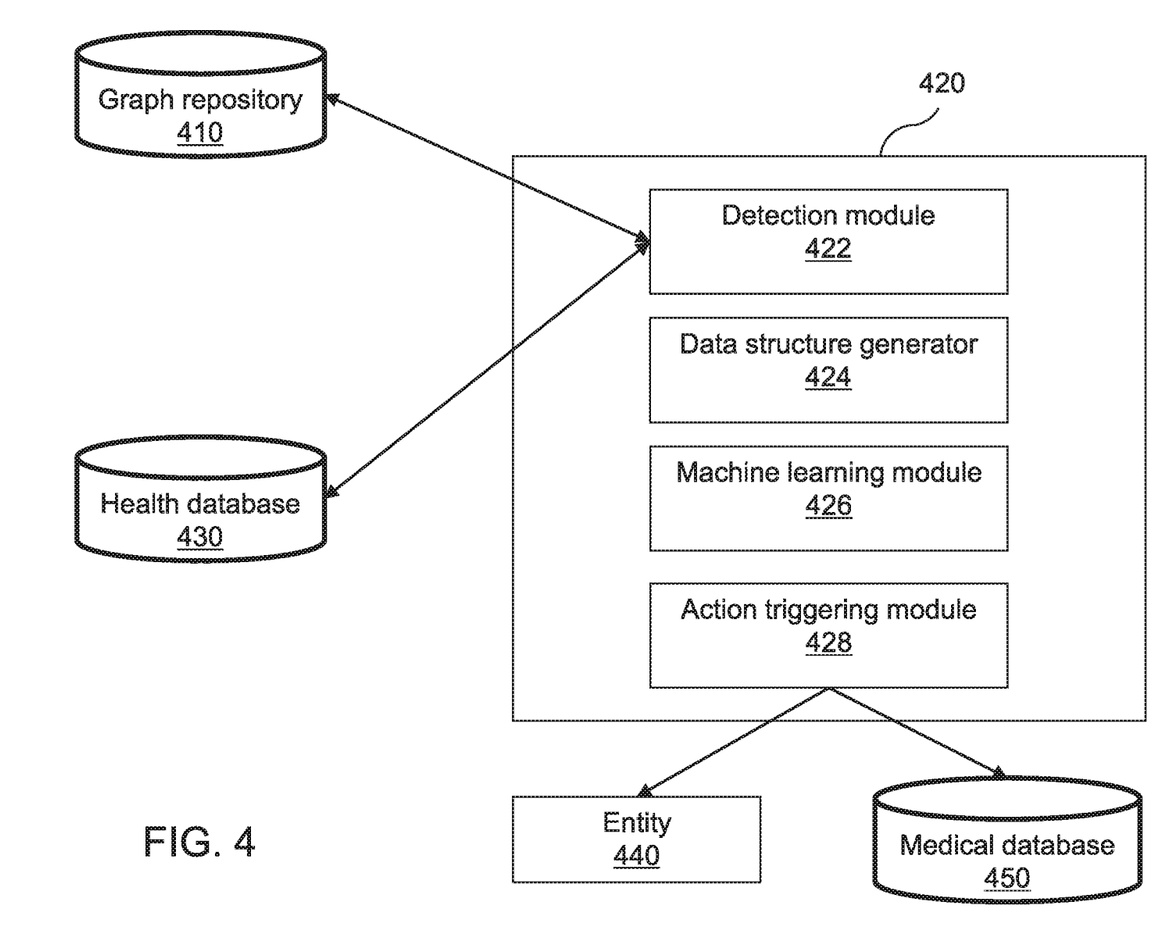
FIG. 4 is a block diagram showing a system for predicting non-communicable disease with infectious risk factors using artificial intelligence, in accordance with an embodiment of the present invention.

With reference to FIG. 4, a block diagram is provided illustrating an overview of a system 400 for predicting non-communicable disease (NCD) with infectious risk factors, in accordance with an embodiment of the present invention. Although the embodiments described herein will be described with reference to predicting NCD with infectious risk factors, the system 400 of FIG. 4 can be embodied within a disease prediction system that uses artificial intelligence and machine learning to predict the occurrence or likelihood of disease based on one or more factors.

The system 400 includes a graph repository 410. The graph repository 410 stores one or more graphs associated with one or more people. For example, the one or more graphs can include one or more graphs associated with one or more respective person-to-person links. The graph includes nodes and edges, where each of the nodes can represent a person and each of the edges can represent a person-to-person link. For example, in one embodiment, each of the nodes can represent a person with a feature vector and NCD onset label, and each of the edges can represent a person-to-person link with a corresponding relationship vector. In one embodiment, the one or more graphs include one or more social network graphs. For example, the one or more social network graphs can be obtained over at least one network based on data derived from one or more social networks.

In the field of machine learning, a feature is an individual measurable property or characteristic being observed, and sets of features can be described by a feature vector. A feature vector is an n-dimensional vector of features that represent one or more objects. Feature vectors function to numerically represent their corresponding objects in order to perform some machine learning task on the objects. An example of a feature vector will now be described with reference to FIG. 5.

Figure 5:
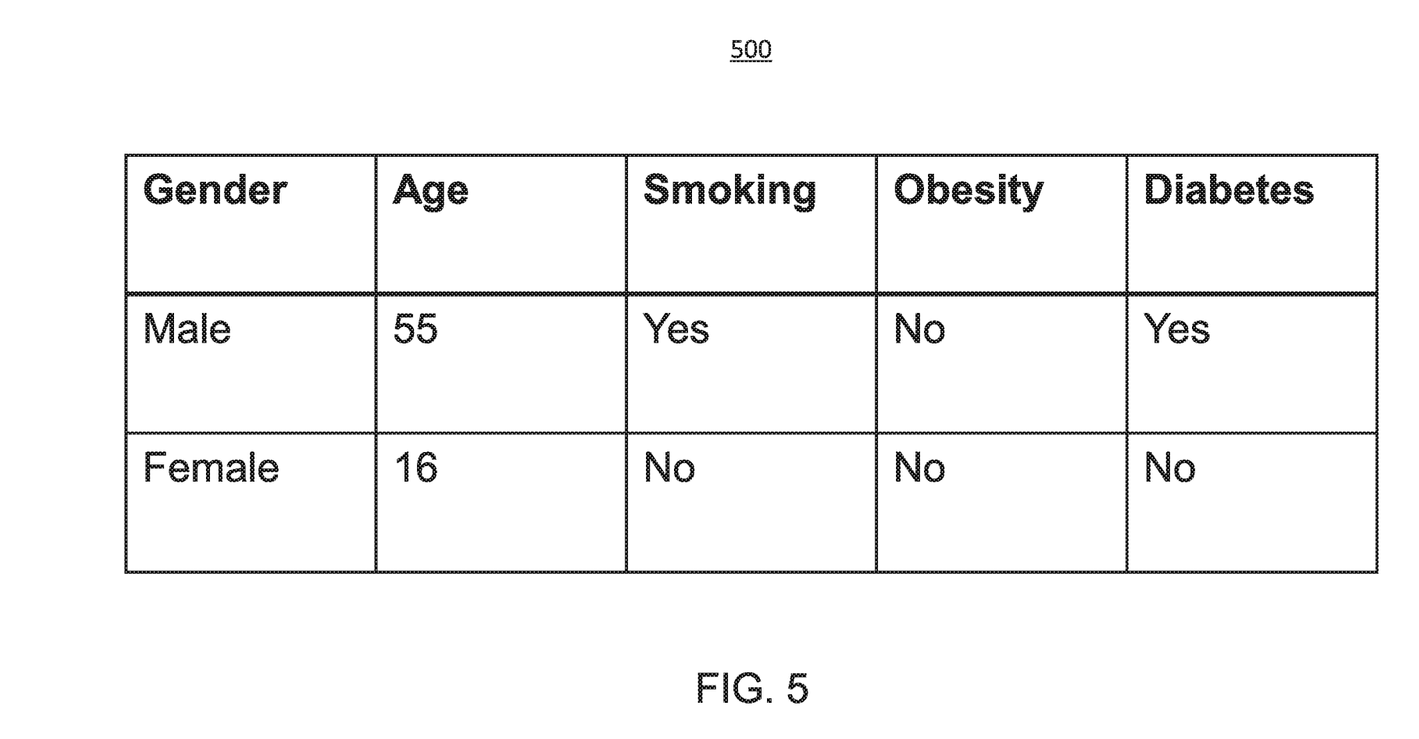
FIG. 5 is a diagram showing an illustrative feature vector, in accordance with an embodiment of the present invention.

With reference to FIG. 5, at least a portion of an illustrative feature vector 500 is shown. The feature vector 500 includes entries corresponding to a 55 year old male and a 16 year old female. The male can illustrative be the father of the female. In this example, the NCD corresponds to diabetes, and the feature vector 500 includes features that correspond to "infectious" risk factors for diabetes such as, e.g., smoking and obesity. As shown, the male smokes, is obese, and has diabetes, while the female does not smoke, is not obese, and does not have diabetes. Although only two people and two risk factors are shown in this illustrative example, any number of people and risk factors can be represented by the feature vector. For example, other family members such as, e.g., a mother, daughter, etc. can be represented.

Referring back to FIG. 4, the relationship vector between two people can be a vector that model one or more types of relationships that exist between the two people. A value of "1" can correspond to the existence of a given relationship type represented within the relationship vector, and a value of "0" can correspond to the lack of the given relationship type. An illustrative relationship vector between two people can be represented as <1, 0, . . . , 1>, where the first value can correspond to a familial relationship, the second value can correspond to a collegial relationship, and the last value can correspond to a friendship relationship. Therefore, in this non-limiting illustrative example, the two people have a familial relationship and a friendship relationship, but not a collegial relationship.

The system 400 further includes an NCD risk predictor 420. The NCD risk predictor 420 can include a detection module 422, a data structure generator 424, a machine learning module 426, and an action triggering module 428.

The detection module 422 is configured to, in response to receipt of a graph associated with a person from the graph repository 410, detect one or more risk factors associated with an NCD based on the graph. The detection module 432 can be implemented to detect the one or more risk factors by searching electronic documents (e.g., electronic versions of academic or medical papers) via one or more electronic databases or repositories, such as health database 430, and identifying the one or more risk factors from one or more electronic documents. One example of a website that can be used to detect one or more risk factors is PubMed, which is a free search engine maintained by the United States National Library of Medicine (NLM) at the National Institutes of Health (NIH) that can access one or more electronic databases (e.g., the Medical Literature Analysis and Retrieval System Online (MEDLINE) database). A relevant keyword search (e.g., a search for "factors spread in large social network") can be performed to identify results for extraction using one or more data mining techniques. For example, if "alcohol" and "loneliness" are included in the results of the keyword search, "alcohol" and "loneliness" can be extracted from the results. Various data mining techniques can be used to mine data. Illustrative, queries can be passed to a website (e.g., PubMed) and the response can then be processed directly in a corresponding programing environment. The code can be automated to build systematic queries with different keywords.

The data structure generator 424 is configured to, for each risk factor, generate a data structure for compactly representing the graph to compute at least one person-to-person distance is generated. In one embodiment, the at least one person-to-person distance is computed based on features vectors of at least two persons and their corresponding relationship vector.

An adjacency matrix is a square matrix used to represent a graph. The elements of the adjacency matrix can indicate whether pairs of vertices are adjacent or not in the graph. In the case of an undirected graph, the adjacency matrix is a symmetric matrix (e.g., the adjacency matrix is equal to its transpose). In the case of a simple graph (e.g., an unidirectional graph without loops or multiple edges), the adjacency matrix can be represented as a Boolean matrix (e.g., (0, 1)-matrix) with "0"s across the diagonal. In the case of a directed graph, the adjacency matrix can be represented as a non-symmetric matrix.

Each element of the adjacency matrix provides a numerical value associated with connection(s) (e.g., edge(s)) between respective pairs of vertices. For example, for a simple graph with a set of vertices V, the adjacency matrix A is a square matrix with dimensions |V|×|V|. Each element of the adjacency matrix A can be represented as $A_{i,j}^k$, where i and j are respective vertices and k represents an index corresponding to the one or more detected risk factors. That is, for a kth detected risk factor, a corresponding adjacency matrix is generated to calculate a person-to-person distance between people corresponding to vertices i and j with respect to the k-th detected risk factor.

As mentioned, the adjacency matrix described herein is a data structure for representing the graph for use by a computer to perform machine learning and/or artificial intelligence tasks, such as those described in further detail below. Because each entry in the adjacency matrix only requires a single bit, the adjacency matrix can be represented in a compact way. For example, an undirected graph can be represented by, e.g., $|V|^2/16$ bytes, and a directed graph can be represented by, e.g., $|V|^2/8$ bytes. In addition to reducing wasted space, due to the compactness of the adjacency matrix, the adjacency matrix can promote or encourage locality of reference. Locality of reference is a property of memory access patterns associated with the accessing of identical values or related memory locations. General types of reference locality include temporal locality and spatial locality. Temporal locality can refer to temporal proximity between references to the same memory location, while spatial locality can refer to the likelihood that memory location(s) nearby a presently memory location will be referenced in the near future. Accordingly, the adjacency matrix described herein is a type of data structure designed to improve the way a computer stores and retrieves data in memory.

The machine learning module 426 is configured to perform metric learning to calculate at least one person-to-person distance based on the adjacency matrix, and perform a machine learning technique on the graph with regularization of the at least one person-to-person distance.

Metric learning is an area of supervised machine learning in the field of artificial intelligence that is used to learn a metric or distance function over objects. Generally, metric learning can be performed to measure how similar or related two objects are based on distance. For example, the person-to-person distance between people i and j corresponding to the k-th detected risk factor, $d_A^k(X_i, X_j, R_{ij})$, can be calculated based on the adjacency matrix $A_k$ using the following equation:

$$d_A^k(X_i,X_j,R_{ij}) = \sqrt{<(X_i-X_j),R_{ij}>^T A^k <(X_i-X_j),R_{ij}>}$$

In the above-equation, $X_i$ represents the feature vector of person i, $X_j$ represents the feature vector of person j, and $R_{ij}$ represents the relationship vector between people i and j.

The machine learning technique can be performed for the nodes of the graph with risk factors and NCD onset labels. In one embodiment, the machine learning technique includes a supervised learning technique. In machine learning, regularization refers to a technique used to solve an ill-posed problem or to prevent overfitting in statistical models. An overfitted statistical model is one that includes more parameters than can be justified by the data or is more complex than is optimal, and thus can fail to fit additional data or reliably predict future observations. Accordingly, regularization allows for improved artificial intelligence modeling. For example, the machine learning technique can implement the following equation implementing regularization:

$$L = L_0 + \Sigma_k \lambda_k L_{reg}^k, \text{ where}$$

$$L_0 = \Sigma_i \|f(X_i), Y_i\|^2, \text{ and}$$

$$L_{reg}^k = \Sigma_{i,j} A_{i,j}^k \|f(X_i) - f(X_j)\|^2.$$

In the above equation, $L_0$ refers to an initial value for regularization, $\lambda_k$ refers to the k-th regulated weight, $L_{reg}^k$ refers to the k-th regularization term, $f(X_i)$ and $f(X_j)$ refer to the predicted scores for people i and j, respectively, $Y_i$ refers to the NCD onset label for person i, and $A_{i,j}^k$ refers to the adjacency matrix for the k-th detected risk factor The action triggering module 428 is configured to trigger one or more actions in response to a determination that a person is at risk of developing an NCD. In one embodiment, triggering the one or more actions can include transmitting, over a network to one or more entities (e.g., entity 440), one or more alerts or messages that the person is at risk of developing an NCD. In another embodiment, triggering the one or more actions can include creating or updating one or more databases associated with the person (e.g., medical database 450).

For example, the one or more entities can include one or more electronic devices associated with the person (e.g., personal computer, tablet, smartphone, Internet of Things (IoT) device). This can allow the person to be actively informed of the NCD at risk of being developed based on the risk factors. Such knowledge can motivate the person to make positive lifestyle changes to mitigate the effects of the risk factors and the development of the NCD. Data related to the alert or message can be used to create and/or update one or more databases associated with the person.

As another example, the one or more entities can include one or more medical providers (e.g., doctors) associated with the person. For instance, an alert or message regarding the risk of developing NCD can be linked to the person's medical records. Such an alert can notify the medical provider(s) to monitor the person for the development of the NCD. In addition, such an alert can also be used by the medical provider(s) to perform testing on the person to identify any possible symptoms of the NCD, and to initiate a course of treatment in response to identifying any symptoms of the NCD. Data related to the alert or message can be used to create and/or update one or more databases associated with the one or more medical providers associated with the person, thereby allowing the one or more medical providers to maintain real-time updates of the person's medical history.

As yet another example, the one or more entities can include one or more medical insurance providers associated with the person. For instance, if the person is determined to be at risk of developing an NCD, the one or more medical insurances provider can use this information in the calculation of a premium for the person based on a likelihood of developing the NCD in the future. Data related to the alert or message can be used to create and/or update one or more databases associated with the one or more medical insurance providers associated with the person, thereby allowing the one or more medical insurance providers to maintain real-time updates of the person's medical history.

Figure 6:
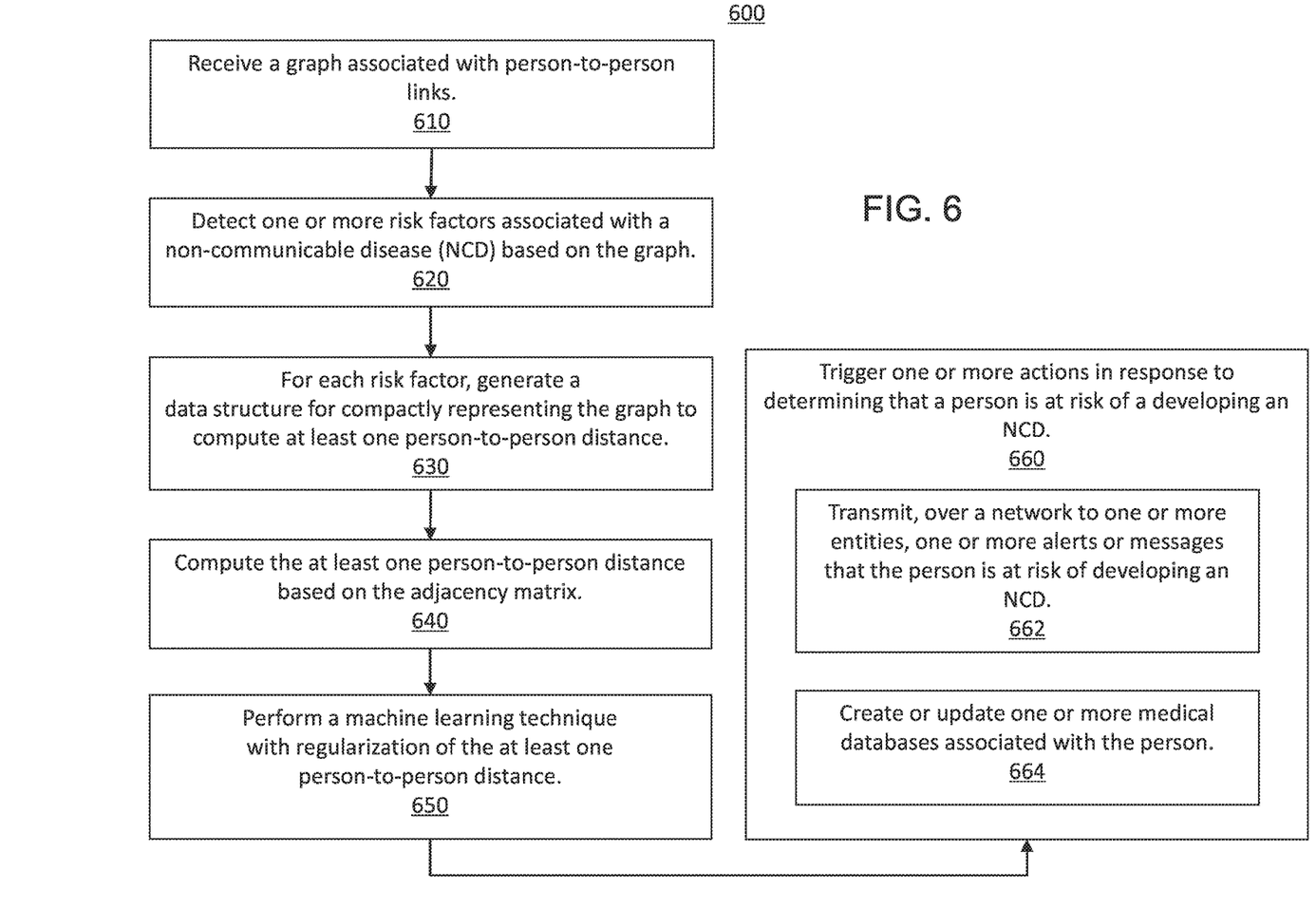
FIG. 6 is a block/flow diagram showing a system/method for predicting non-communicable disease with infectious risk factors using artificial intelligence, in accordance with an embodiment of the present invention.

With reference to FIG. 6, a block/flow diagram is provided illustrating an overview of a system/method 600 for predicting non-communicable disease (NCD) with infectious risk factors, in accordance with an embodiment of the present invention.

At block 610, a graph associated with person-to-person links is received. In one embodiment, the graph includes a social network graph. The graph includes nodes and edges. For example, in one embodiment, each of the nodes can represent a person with a feature vector and NCD onset label, and each of the edges can represent a person-to-person link with a corresponding relationship vector. Further details regarding block 610 are described above with reference to FIGS. 4-5.

At block 620, one or more risk factors associated with the NCD are detected based on the graph. The one or more risk factors can be detected using a detector that can be implemented to search electronic documents (e.g., electronic versions of academic or medical papers) via one or more electronic databases or repositories, and identify the one or more risk factors from one or more electronic documents. One example of a website that can be used to detect one or more risk factors is PubMed, which is a free search engine maintained by the United States National Library of Medicine (NLM) at the National Institutes of Health (NIH) that can access one or more electronic databases (e.g., the Medical Literature Analysis and Retrieval System Online (MEDLINE) database). A relevant keyword search (e.g., a search for "factors spread in large social network") can be performed to identify results for extraction using one or more data mining techniques. For example, if "alcohol" and "loneliness" are included in the results of the keyword search, "alcohol" and "loneliness" can be extracted from the results. Various data mining techniques can be used to mine data. Illustrative, queries can be passed to a website (e.g., PubMed) and the response can then be processed directly in a corresponding programing environment. The code can be automated to build systematic queries with different keywords.

At block 630, for each risk factor, a data structure for compactly representing the graph is generated to compute at least one person-to-person distance is generated. In one embodiment, the at least one person-to-person distance is computed based on features vectors of at least two persons and their corresponding relationship vector. The data structure can illustratively include an adjacency matrix. As describe above with reference to FIG. 4, the adjacency matrix described herein is a data structure for representing the graph for use by a computer to perform machine learning and/or artificial intelligence tasks, sand is a type a type of data structure designed to improve the way a computer stores and retrieves data in memory. Further details regarding block 630 are described above with reference to FIG. 4.

At block 640, metric learning is performed to calculate at least one person-to-person distance based on the adjacency matrix and, at block 650, a machine learning technique is performed on the graph with regularization of the at least one person-to-person distance. The machine learning technique can be performed for the nodes of the graph with risk factors and NCD onset labels. In one embodiment, the machine learning technique includes a supervised learning technique. Further details regarding blocks 640 and 650 are described above with reference to FIG. 4.

At block 660, one or more actions can be triggered in response to determining that a person is at risk of developing an NCD. In one embodiment, at block 662, triggering the one or more actions can include transmitting, over a network to one or more entities, one or more alerts or messages that the person is at risk of developing an NCD. In another embodiment, at block 664, triggering the one or more actions can include creating or updating one or more medical databases associated with the person. Further details regarding blocks 660-664 are described above with reference to FIG. 4.

Having described preferred embodiments of a system and method for predicting non-communicable disease with infectious risk factors using artificial intelligence (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for predicting non-communicable diseases with infectious risk factors using artificial intelligence, comprising:
   detecting one or more risk factors associated with a non-communicable disease based on a graph associated with person-to-person links;
   reducing wasted storage space and promoting locality of reference by, for each risk factor, generating a data structure including an adjacency matrix having a compactness using single bit entries for compactly representing the person-to-person links in the graph to compute at least one person-to-person distance using the adjacency matrix;
   performing a machine learning technique with regularization of the at least one person-to-person distance to predict the non-communicable disease with infectious risk factors; and
   initiating a course of medical treatment responsive to an affirmative prediction.

2. The method of claim 1, wherein the graph includes a social network graph.

3. The method of claim 1, wherein each node of the graph represents a person having a corresponding feature vector and non-communicable disease onset label, and wherein each edge of the graph represents a person-to-person link with a relationship vector.

4. The method of claim 3, further comprising computing the at least one person-to-person distance using metric learning based on feature vectors of at least two persons and their corresponding relationship vector.

5. The method of claim 1, wherein the one or more risk factors are detected using a detector to perform a relevant keyword search to identify results for extraction using one or more data mining techniques.

6. The method of claim 1, further comprising triggering one or more actions in response to determining that a person is at risk of developing a non-communicable disease.

7. A system for predicting non-communicable diseases with infectious risk factors using artificial intelligence, comprising:
   a memory device for storing program code; and
   at least one processor operatively coupled to the memory device and configured to execute program code stored on the memory device to:
      detect one or more risk factors associated with a non-communicable disease based on a graph associated with person-to-person links;
      reduce wasted storage space and promoting locality of reference by, for each risk factor, generating a data structure including an adjacency matrix having a compactness using single bit entries for compactly representing the person-to-person links in the graph to compute at least one person-to-person distance using the adjacency matrix;
      perform a machine learning technique with regularization of the at least one person-to-person distance to predict the non-communicable disease with infectious risk factors; and
      initiating a course of medical treatment responsive to an affirmative prediction.

8. The system of claim 7, wherein the graph includes a social network graph.

9. The system of claim 7, wherein each node of the graph represents a person having a corresponding feature vector and non-communicable disease onset label, and wherein each edge of the graph represents a person-to-person link with a relationship vector.

10. The system of claim 9, wherein the at least one processor is further configured to execute program code stored on the memory device to compute the at least one person-to-person distance using metric learning based on feature vectors of at least two persons and their corresponding relationship vector.

11. The system of claim 7, wherein the at least one processor is further configured to detect the one or more risk factors using a detector to perform a relevant keyword search to identify results for extraction using one or more data mining techniques.

12. The method of system of claim 7, wherein the at least one processor is further configured to trigger one or more actions in response to determining that a person is at risk of developing a non-communicable disease.

13. A computer program product comprising a non-transitory computer readable storage medium having program instructions embodied therewith, the program instructions executable by a computer to cause the computer to perform a method for predicting non-communicable diseases with infectious risk factors using artificial intelligence, the method performed by the computer comprising:
    detecting one or more risk factors associated with a non-communicable disease based on a graph associated with person-to-person links;
    reducing wasted storage space and promoting locality of reference by, for each risk factor, generating a data structure including an adjacency matrix having a compactness using single bit entries for compactly representing the person-to-person links in the graph to compute at least one person-to-person distance using the adjacency matrix;
    performing a machine learning technique with regularization of the at least one person-to-person distance to predict the non-communicable disease with infectious risk factors; and
    initiating a course of medical treatment responsive to an affirmative prediction.

14. The computer program product of claim 13, wherein each node of the graph represents a person having a corresponding feature vector and non-communicable disease onset label, and wherein each edge of the graph represents a person-to-person link with a relationship vector.

15. The computer program product of claim 14, wherein the method further comprises computing the at least one person-to-person distance using metric learning based on feature vectors of at least two persons and their corresponding relationship vector.

16. The computer program product of claim 13, wherein the one or more risk factors are detected using a detector to perform a relevant keyword search to identify results for extraction using one or more data mining techniques.

17. The computer program product of claim 13, wherein the method further comprises triggering one or more actions in response to determining that a person is at risk of developing a non-communicable disease.

* * * * *